United States Patent [19]

Tosa et al.

[11] Patent Number: 5,342,785
[45] Date of Patent: Aug. 30, 1994

[54] METHOD FOR DETERMINING PYROGEN CONTENT

[75] Inventors: Tetsuya Tosa, Kyoto; Tadashi Sato, Takatsuki; Taizo Watanabe, Nagaokakyo; Satoshi Minobe, Otsu, all of Japan

[73] Assignee: Tanabe Seiyaku Co., Ltd., Osaka, Japan

[21] Appl. No.: 141,689

[22] Filed: Oct. 26, 1993

Related U.S. Application Data

[63] Continuation of Ser. No. 876,829, Apr. 30, 1992, abandoned, which is a continuation of Ser. No. 374,819, Jul. 3, 1989, abandoned.

[30] Foreign Application Priority Data

Jul. 5, 1988 [JP] Japan .................... 63-168063
Oct. 28, 1988 [JP] Japan .................... 63-274249

[51] Int. Cl.$^5$ .................................. G01N 33/00
[52] U.S. Cl. .............................. 436/178; 436/86; 436/501; 436/503
[58] Field of Search ............ 436/86, 501–502, 436/178; 435/34; 210/651, 692

[56] References Cited

U.S. PATENT DOCUMENTS

| | | |
|---|---|---|
| 3,944,391 | 3/1976 | Harris et al. |
| 4,059,512 | 11/1977 | Harris .................... 210/692 |
| 4,276,050 | 6/1981 | Firca et al. ............. 436/502 |
| 4,381,239 | 4/1983 | Chibata et al. ........ 210/692 |
| 4,394,487 | 7/1983 | Müller et al. ......... 525/281 |
| 4,430,229 | 2/1984 | Yamawaki et al. ... 210/263 |
| 4,476,093 | 10/1984 | Watanabe et al. ... 436/502 |
| 4,510,241 | 4/1985 | Mills ...................... 436/502 |
| 4,663,163 | 5/1987 | Hou et al. .............. 210/635 |
| 4,677,194 | 6/1987 | Hoa ........................ 530/350 |
| 4,740,460 | 4/1988 | Sakata et al. .......... 436/502 |

FOREIGN PATENT DOCUMENTS 2092470 8/1982 United Kingdom .

OTHER PUBLICATIONS

Kawaski, Konoshin; "Detection of Bacterial Endotoxin in Water Samples by Limulus Amebocyte Lysate Method" Bokin Bobai 17(5) 221–7, 1989.

Zimmermann, G.; Kiltz, R.; Krueger, D., "Removal of Interfering Substances with Disposable Ultrafillers in Endotoxin Determination by Means . . . Limulus Test" Drugs Made Ger. 31(3) 96–100, 1988.

*Primary Examiner*—Lyle A. Alexander
*Attorney, Agent, or Firm*—Browdy and Neimark

[57] ABSTRACT

A method for determination of a pyrogen content which comprises bringing a specimen into contact with an adsorbent composed of a nitrogen-containing heterocyclic compound bonded to a water-insoluble carrier directly or through a spacer, and after or without eluting the pyrogen adsorbed on the adsorbent, determining the content of the adsorbed pyrogen by the Limulus method.

5 Claims, 3 Drawing Sheets

LPS CONCENTRATION (pg/ml)

LPS CONCENTRATION (pg/ml)

METHOD FOR DETERMINING PYROGEN CONTENT

CROSS-REFERENCE TO RELATED APPLICATIONS

The present application is a continuation of application Ser. No. 07/876,829, filed Apr. 30, 1992, now abandoned, which was a continuation of application Ser. No. 07/374,819, filed Jul. 3, 1989, now abandoned.

FIELD OF THE INVENTION

The present invention relates to a method for determination of a pyrogen content. More particularly, it relates to a method for determination of a pyrogen content which is applicable to even a specimen which has hitherto been difficult to determine because of the presence of determination interfering substances and the like.

BACKGROUND OF THE INVENTION

Pyrogens are pyrogenetic substances which abnormally raise the body temperature of a homothermic animal in a very small amount. When a pyrogen is introduced into the human body, for example, by intravenous injection of a medicine contaminated with it, apart from the main activity of the medicine, the pyrogen causes severe fever. It is said that, when this action of pyrogen becomes serious, it causes severe fever accompanied with chill and shudder and, occasionally, death from a shock. Many substances such as bacterial substances, inflammatory substances, plant polysaccharides, blood group substances and the like have been known as pyrogens. Among them, bacterial substances have the most important influence on fever and are called as bacterial toxins. In general, bacterial toxins are classified into exotoxins and endotoxins. Particularly, it is said that an endotoxin acting as so-called O-antigen the main component of which is a cell wall lipopolysaccharide (LPS) of a gram negative bacterium has the strongest pyrogenicity.

Accordingly, it is very important to detect or determine a pyrogen content, for example, to prevent contamination of a pyrogen in the production of medicines.

As a method for detecting or determining a pyrogen content, for example, there has been hitherto known fever test using a rabbit, or Limulus test using a blood cell extract of *Limulus polyphenus*. Particularly, Limulus test has been often used from viewpoints of sensitivity, simplicity, quantitative properties and the like.

However, Limulus test is liable to be interfered or activated by various substances present during determination and, therefore, complicated pre-treatment is required or, sometimes, it becomes difficult to determine the pyrogen content depending upon a specimen. Further, there are some substances other than pyrogens which are positive in Limulus test and they interfere precise determination of the pyrogen content. In order to solve this problem, it has been proposed to use highly purified reagents. However, such reagents are very expensive. Further, it is considered to be difficult to determine a very small amount of pyrogens contained in a substance having a low solubility.

Recently, in order to detect an endotoxin which is one of pyrogens, there has been proposed a method which comprises bringing a pyrogen-free activated charcoal obtained by treatment with an acid into contact with a specimen and reacting the activated charcoal with Limulus lysate to carry out Limulus test easily and rapidly (Japanese Patent Laid Open Publication No. 152425/1981). However, this method is yet unsatisfactory from viewpoints of specificity, sensitivity and quantitative properties for pyrogens. Further, U.S. Pat. No. 4,491,660 discloses that a certain polymer which can adsorbs an endotoxin can be used for concentrating and detecting the endotoxin. However, this polymer is yet unsatisfactory from viewpoints of specificity, sensitivity and quantitative properties for pyrogens, too.

The present inventors have already found that pyrogens are specifically adsorbed by an adsorbent comprising a nitrogen-containing heterocyclic compound bonded to a water-insoluble carrier directly or through a spacer and has filed a patent application (Japanese Patent Laid Open Publication No. 183712/1982). Then, the present inventors have further studied and found that, by using such an adsorbent, a pyrogen content can be readily carried out by Limulus test in high specificity and sensitivity even in the presence of various interfering substances or other Limulus test positive substances.

OBJECTS OF THE INVENTION

The main object of the present invention is to provide an improved method for determination of a pyrogen content by Limulus test.

This object as well as other objects and advantages of the present invention will become apparent to those skilled in the art from the following description with reference to the accompanying drawings.

SUMMARY OF THE INVENTION

Figure 1:
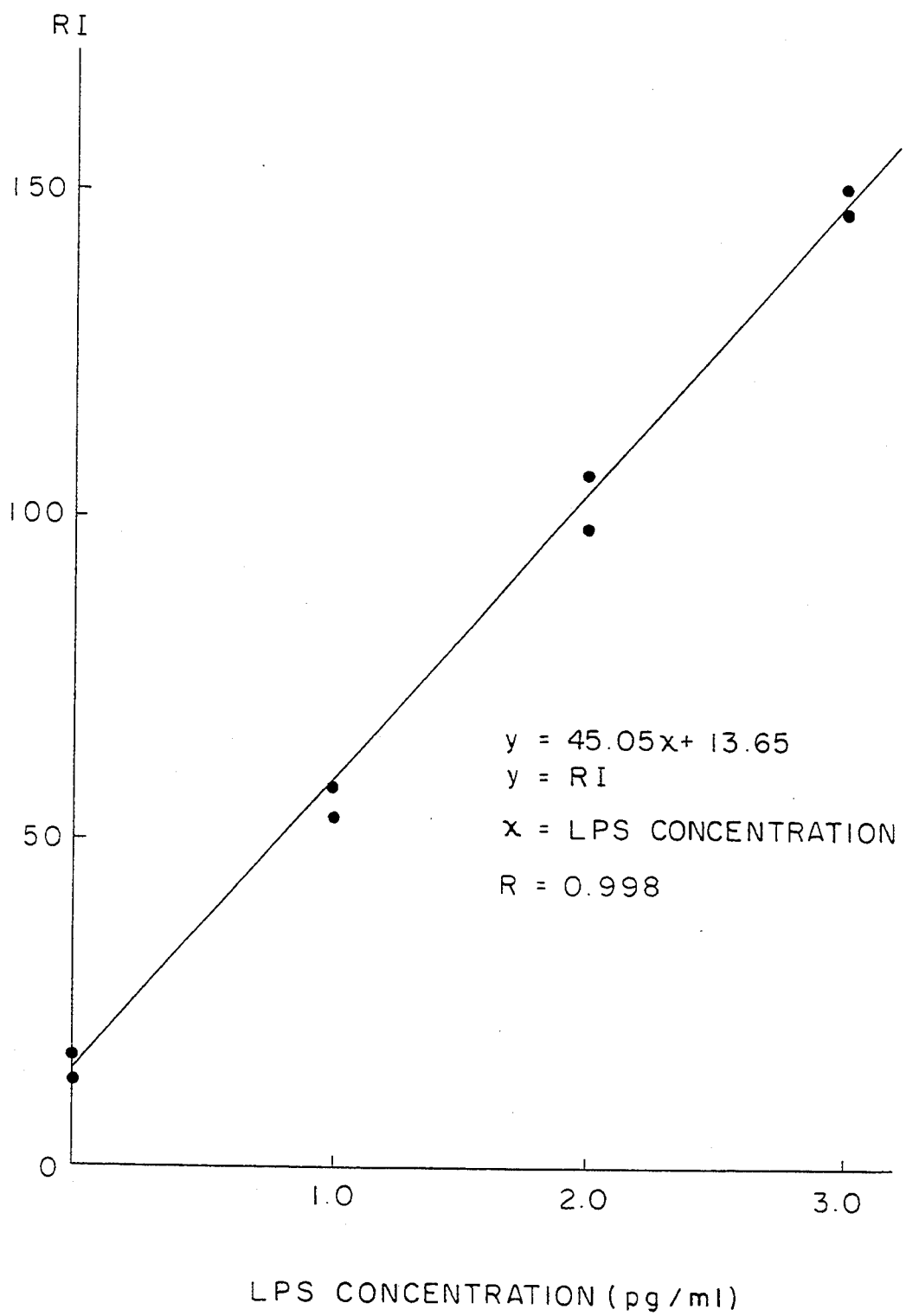
FIGS. 1 to 3 are examples of calibration curves used in the determination of the present invention, respectively.

According to the present invention, there is provided a method for determination of a pyrogen content which comprises bringing a specimen into contact with an adsorbent composed of a nitrogen-containing heterocyclic compound bonded to a water-insoluble carrier directly or through a spacer, and after or without eluting the pyrogen adsorbed on the adsorbent, determining the pyrogen content of the adsorbed pyrogen by means of Limulus method.

DETAILED DESCRIPTION OF THE INVENTION

The adsorbent to be used in the present invention may be that disclosed in the above present inventors' Japanese Patent Laid Open Publication No. 183712/1982. Examples of the adsorbent are those wherein the nitrogen-containing heterocyclic compound is represented by the general formula:

$$R—A—X \qquad [I]$$

wherein R is a nitrogen-containing heterocyclic group having nitrogen atom as a hetero atom; A is a single bond, an alkylene group or an alkenylene group; X is hydrogen or a functional group when A is a single bond, or a functional group when A is an alkylene group or an alkenylene group; and the heterocyclic group and alkylene group may be substituted with one or more substituents, the water-insoluble carrier is that having hydroxy, amino, carboxyl or a halogen atom, and
the spacer is a compound of formula:
$NH_2(CH_2)_nNH_2$,
$NH_2(CH_2)_nCOOH$,
$NH_2(CH_2)_nOH$, or
$HOOC(CH_2)_nCOOH$ wherein n is an integer oif 1 to 12.

Examples of the nitrogen-containing heterocyclic compound of the formula [I] include those wherein R is a nitrogen-containing heterocyclic group having, for example, imidazole nucleus, pyrazole nucleus, pyrimidine nucleus, pyridazine nucleus, pyrazine nucleus, purine nucleus, acridine nucleus, triazole nucleus, oxadiazole nucleus, tetrazole nucleus, indazole nucleus, benzotriazole nucleus, benzopyridazine nucleus, benzopyrimidine nucleus, benzopyrazine nucleus or naphthyridine nucleus; A is a single bond and X is hydrogen or a functional group such as amino, hydroxy or carboxy, or A is an alkylene group having 1 to 12 carbon atoms such as methylene, ethylene, propylene, butylene, hexylene, octylene, decamethylene or dodecamethylene or an alkenylene group having 2 to 12 carbon atoms such as vinylene, propylene, butenylene, hexenylene or octenylene and X is a functional group such as amino, hydroxy or carboxyl. The nitrogen-containing heterocyclic group of R and the alkylene group of A may be optionally substituted with one or more substituents (e.g. carboxyl, oxo, alkyl having 1 to 4 carbon atoms, hydroxy, amino, alkoxy having 1 to 4 carbon atoms, etc.). Preferred examples of the nitrogen-containing heterocyclic compounds are those of the formula [I] wherein R is a nitrogen-containing heterocyclic group having imidazole nucleus, pyrimidine nucleus, purine nucleus or acridine nucleus, A is a single bond, ethylene or ethylene substituted with carboxyl, and X is amino, carboxy or hydroxy.

As the water-insoluble carrier, any water-insoluble carrier which can be bonded to the nitrogen-containing heterocyclic compound of the general formula [I] directly or through a spacer can be used in the present invention. Representative examples of the water-insoluble carrier include those having hydroxy, amino, carboxyl or a halogen atom. Preferred examples of the water-insoluble carrier having hydroxy are polysaccharides (e.g. cellulose, agarose, cross-linked dextran, etc.), hydroxyalkylated polystyrene resins (e.g. hydroxyalkylated styrene-divinylbenzene copolymer, etc.), polyvinyl alcohol or the like. Examples of the water-insoluble carrier having amino group are aminoalkylated polysaccharides (e.g. aminoalkylated celluloses such as aminoethylcellulose or aminohexylcellulose, aminoalkylated agarose such as aminohexylagarose, a p-aminobenzylated polysaccharides (e.g. p-aminobenzylcellulose, p-aminobenzylagarose, etc.), chitosan, aminoalkylated polystyrene resins (e.g. aminoalkylated styrene-divinylbenzene copolymer, etc.), polyacrylamides, aminoalkylated polyacrylamides (e.g. aminoethylpolyacrylamide, etc.), aminoalkylated porous glass (e.g. aminopropyl porous glass, etc.) and the like. Examples of the water-insoluble carrier having carboxyl group are carboxyalkylated polysaccharides (e.g. carboxyalkylated agarose such as carboxyhexylagarose or carboxypentylagarose, carboxyalkylated celluloses such as carboxymethylcellulose, carboxyalkylated cross-linked dextran such as carboxymethyl-crosslinked dextran, etc.), carboxylic acid resins (e.g. acrylic acid-divinylbenzene copolymer, etc.) and the like. Examples of the water-insoluble carrier having a halogen atom are halogenoalkylpolystyrene resins (e.g. chloromethylated styrene-divinylbenzene copolymer, etc.) and the like.

Preferred examples of the adsorbent used in the present invention are those obtained by bonding the nitrogen-containing heterocyclic compound [I] such as histidine, histamine, urocanic acid, uracil, orotic acid, cytosine, 5-methylcytosine, 2-amino-4,6-dimethylpyrimidine, 2-amino-4-hydroxy-6-methylpyrimidine, adenine or 6,9-diamino-2-ethoxyacridine to the water-insoluble polysaccharide through alkylenediamine as the spacer by using, at least, either one of a monoepoxide (e.g. epichlorohydrin, etc.) and an aliphatic dialdehyde (e.g. glutaraldehyde, etc.).

Further preferred examples of the adsorbent used in the present invention are those obtained by bonding histidine or histamine to a water-insoluble polysaccharide (e.g., cellulose or agarose) through an alkylenediamine by epichlorohydrin.

The adsorbent used in the present invention is characterized in that it specifically adsorbs only pyrogens. Thus, the method of the present invention can be carried out by bringing the adsorbent into contact with a specimen to adsorb a pyrogen in the specimen, washing the specimen to remove substances other than the pyrogen, after or without eluting the adsorbed pyrogen, subjecting it to a conventional Limulus test to determine the pyrogen content.

In the method of the present invention, the specimen to be examined should be used in a solution state, for example, a water-containing solution or an aqueous solution state and, particularly, an aqueous solution state is preferred. The adsorbent used in the present invention does not adsorb interfering substances, for example, amino acids (e.g. L-cysteine, etc.), antibiotics (e.g. penicillin G, streptomycine, etc.), protein denaturants (e.g. urea, etc.), serine protease inhibitors (e.g. diisopropylfluorophosphoric acid, etc.), saccharides (e.g. glucose, etc.), sugar alcohols, sodium chloride, Ringer's solution and the like. The adsorbent does not adsorb Limulus test positive substances other than pyrogens, for example, polysaccharides such as dextran, $(1\rightarrow 3)$-$\beta$-D-glucan and the like, either. Therefore, the method of the present invention can also be applied to a specimen containing these substances which have hitherto been difficult to determine the pyrogen content.

The adsorption operation of the pyrogen can be carried out by bringing the specimen into contact with the adsorbent, for example, by mixing and stirring a specimen with an adsorbent in a container or by passing the specimen through a column packed with the adsorbent. The conditions of the adsorption operation can be appropriately selected according to a particular specimen. Usually, the pyrogen can be specifically and efficiently adsorbed by using 3 to 100 mg, preferably 7 to 40 mg of the adsorbent per 1 ml of the specimen and carrying out the adsorption under conditions of a temperature of 4° to 40° C., pH of 4 to 8, preferably, 6 to 7 and an ionic strength of not more than 0.1, preferably 0 to 0.05. Under such conditions, by carrying out the adsorption operation for about 30 minutes or longer, the pyrogen in the specimen is almost completely adsorbed on the adsorbent and the pyrogen is condensed on the adsorbent. Further, re-adsorption can also be carried out after completion of adsorption, thereby, sensitivity of determination can be raised.

The adsorbent which has adsorbed the pyrogen is separated from the specimen according to a known method and then, washed with a pyrogen-free water, a pyrogen-free buffer solution or the like to remove substances other than the pyrogen.

In the present invention, the adsorbent thus washed can be directly subjected to Limulus test as it is, or the pyrogen adsorbed can be eluted with, for example, 0.4 M Tris hydrochloride buffer (pH 8.0) containing 0.04 M magnesium chloride according to a known method or the like and then subjected to a conventional Limulus test.

In general, the Limulus test is classified into synthetic substrate method and gelation method and the synthetic substrate method is further classified into colorimetry and fluorimetry according to a particular kind of the substrate. In the present invention, any of these methods can be employed. For example, the adsorbent wherein the pyrogen has been adsorbed or the eluent thereof is reacted with Limulus lysate at 25° to 40° C., usually, 37° C. for 10 to 120 minutes, turbidity of the reaction solution due to gelation is measured with time, and then, the concentration of the pyrogen in the specimen can be determined based on a calibration curve which is made separately by using an authentic sample (e.g. LPS, etc.) according to the same operation as that described above. Alternatively, the adsorbent wherein the pyrogen has been adsorbed or the eluent thereof is reacted with Limulus lysate and a synthetic substrate having a chromophore or fluorophore under the same conditions. After completion of the reaction, the reaction mixture is subjected to colorimetry or fluorimetry and then the pyrogen content in the specimen is determined according to a calibration curve which is made separately according to the same manner as that described above. In the case of colorimetry, the determination can be carried out by using a synthetic substrate, for example, Boc-Leu-Gly-Arg-pNA (wherein Boc is t-butoxycarbonyl and pNA is p-nitroaniline) and measuring the absorbancy at the wavelength of 405 nm. In the case of fluorimetry, the determination can be carried out by using a synthetic substrate, for example, Boc-Leu-Gly-Arg-MCA (wherein Boc is the same as defined above and MCA is 7-amino-4-methylcumarin) and measuring the fluorescence at the excitation wavelength of 380 nm and the fluorescent wavelength of 460 nm.

The adsorbent used in the present invention can be produced, for example, according to the same manner as that described in the above Japanese Patent Laid Open Publication No. 183712/1982.

According to the present invention, determination sensitivity of Limulus test can be extremely improved and the pyrogen content of a specimen even containing interfering substances which has hitherto been considered to be difficult to measure can also be determined. Further, even if Limulus test positive substances other than pyrogens are contained in the specimen, separation and determination of pyrogens can be carried out. Furthermore, it is possible to use a cheaper reagent instead of Limulus reagent. Thus, the method for determination of a pyrogen content of the present invention is suitable for applying to check during the production of medicines and the like.

The following Examples and Reference Examples further illustrate the present invention in detail but are not to be construed to limit the scope thereof.

EXAMPLE 1

Study on calibration curve

To pyrogen-free water (3 ml) was added a predetermined amount of LPS (derived from *E. coli* 0128: B12) to prepare an aqueous LPS solution (concentration of LPS: 0, 1, 2 or 3 pg/ml). To the solution was added the adsorbent prepared in Reference Example 1 hereinafter (30 mg, wet weight) and the mixture was stirred at 50 r.p.m. at room temperature for one hour. Then, it was centrifuged at 3000 r.p.m. for 5 minutes and the precipitated adsorbent was thoroughly washed with pyrogen-free water (3 ml). To the precipitate was added a substrate solution, i.e., an aqueous solution of 0.4 mM Boc-Leu-Gly-Arg-MCA (50 µl) and Limulus amebocyte lysate [prepared by dissolving 1 vial (for 0.2 ml, sensitivity: gelled at 0.1 ng/ml as FDA reference endotoxin EC-2 concentration) of Limulus single test Wako (manufactured by Wako Pure Chemical Industries, Ltd.) into 0.4 M Tris hydrochloride buffer (pH 8.0, 1.5 ml) containing 0.04 M magnesium chloride](50 µl) and the mixture was reacted at 37° C. for 30 minutes. After completion of the reaction, a 12.5% aqueous acetic acid solution (2.3 ml) was added to terminate the reaction and the mixture was centrifuged at 3000 r.p.m. for 5 minutes. Then, fluorimetry was carried out at 380 nm of excitation wavelength and 460 nm of fluorescent wavelength. The results are shown in Table 1.

When the data obtained were plotted on a graph wherein ordinates indicated the relative intensity (RI) in fluorimetry and abscissas indicated LPS concentration to obtain the calibration curve as shown in FIG. 1.

As seen from FIG. 1, the calibration curve shows good linear relationship even in the low LPS concentration region.

TABLE 1

| Run No. | LPS concentration (pg/ml) | RI |
| --- | --- | --- |
| 1 | 0.0 | 13.6 |
| 2 | 0.0 | 17.1 |
| 3 | 1.0 | 54.0 |
| 4 | 1.0 | 59.0 |
| 5 | 2.0 | 99.0 |
| 6 | 2.0 | 107.0 |
| 7 | 3.0 | 148.0 |
| 8 | 3.0 | 152.0 |

EXAMPLE 2

Reproducibility of data obtained by the method of the present invention

To pyrogen-free water (3 ml) was added a predetermined amount of LPS (derived from *E. coli* 0128: B12) was stirred to obtain an aqueous LPS solution containing LPS of 2 pg/ml. According to the same manner as that described in Example 1, LPS content (relative intensity RI in fluorimetry) in the LPS solution or pyrogen-free water (3 ml, corresponding to LPS concentration of 0 pg/ml) was determined by using the adsorbent (30 mg) prepared in Reference Example 1 hereinafter. The results obtained by 4 runs per each solution are shown in Table 2.

TABLE 2

| | Amount of LPS (pg/ml) | |
|---|---|---|
| | 0 | 2 |
| RI | 8.9 | 73.2 |
| | 9.3 | 73.0 |
| | 7.8 | 73.7 |
| | 7.8 | 77.5 |

As is clear from Table 2, when the kind and the content of LPS are constant, the data obtained by the quantitative determination (relative intensity RI in fluorimetry) are also constant. Thus, reproducibility of the method of the present invention is high.

EXAMPLE 3

Applicability of the method of the present invention to various pyrogens

Applicability of the method of the present invention to various pyrogens (LPS) was studied as follows.

(1) Determination of LPS content according to the method of the present invention To pyrogen-free water (3 ml) was added various LPS derived from microorganisms as described in Table 3 to obtain various aqueous LPS solutions having LPS concentrations of 1.25 to 6 pg/ml. According to the same manner as described in Example 1, LPS content in each solution was determined by using the adsorbent (30 mg) prepared in Reference Example 1 hereinafter. Endotoxin units (EU) of various LPS were determined based on LPS content of each specimen solution by using LPS derived from E. coli 0128: B12 (10.4 EU/ng) as the endotoxin standard.

(2) Determination of LPS content according to Limulus method using fluorescent synthetic substrate (control method).

To aqueous solutions of various LPS having a concentrations of 2.5 to 6 pg/ml (100 μl) was added the substrate solution used in Example 1 (50 μl) and Limulus amebocyte lysate used in Example 1 (50 μl), respectively, and the mixture was reacted at 37° C. for 65 minutes. The reaction was terminated by addition of a 12.5% aqueous acetic acid solution (3 ml). Then, according to the same manner as described in Example 1, LPS content was determined by measuring relative intensity in fluorimetry. According to the same manner as described above, endotoxin units of various LPS were determined by using the LPS derived from E. coli 0128: B12 as the endotoxin standard. The results are shown in Table 3 below.

TABLE 3

| LPS | Method of present invention (EU/ng) | Control method (EU/ng) |
|---|---|---|
| LPS derived from E. coli O128: B12 | 10.4 | 10.4 |
| LPS derived from E. coli O111: B4 | 7.9 | 8.0 |
| LPS derived from E. coli O55: B5 | 11.6 | 12.1 |
| LPS derived from E. coli UKT-B | 24.9 | 22.7 |
| LPS derived from Klebsiella pneumoniae | 11.5 | 10.4 |

As is clear from Table 3, the method of the present invention is applicable to determination of content of various LPS as known Limulus method using a fluorescent synthetic substrate.

EXAMPLE 4

Measurement of the concentration of the pyrogen in an aqueous phenylalanine solution To a 2% aqueous phenylalanine solution (30 ml) was added the adsorbent prepared in Reference Example 1 hereinafter (500 mg, wet weight) and the mixture was stirred at 50 r.p.m. at room temperature for 4 hours. Then, the adsorbent was removed to prepare a pyrogen-free aqueous phenylalanine solution.

To this aqueous phenylalanine solution was added LPS (derived from E. coli 0128: B12) so that the concentration of LPS became 1 pg/ml to 2 pg/ml and the mixture was stirred to obtain LPS solution. To the solution (3 ml) was added the adsorbent prepared in Reference Example 1 hereinafter (30 mg, wet weight) and the mixture was stirred at room temperature for one hour. Then, it was centrifuged at 3000 r.p.m. for 5 minutes and the adsorbent precipitated was washed with pyrogen-free phosphate buffer (pH 7.0, $\mu=0.02$) (3 ml). To the precipitate was added an aqueous solution of 0.4 mM Boc-Leu-Gly-Arg-MCA (50 μl) as a substrate solution and Limulus amebocyte lysate [prepared by dissolving 1 vial (for 0.2 ml, sensitivity: gelled at 0.1 ng/ml as FDA reference endotoxin EC-2 concentration) of Limulus single test Wako (manufactured by Wako Pure Chemical Industries, Ltd.) into 0.4 M Tris hydrochloride buffer (pH 8.0, 1.5 ml) containing 0.04 M magnesium chloride] (50 μl) and the mixture was reacted at 37° C. for 30 minutes. After completion of the reaction, a 12.5% aqueous acetic acid solution was added to terminate the reaction and centrifuged at 3000 r.p.m. for 5 minutes. Then, fluorimetry was carried out at 380 nm of excitation wavelength and 460 nm of fluorescent wavelength. The concentration of the pyrogen was determined by the relative intensity based on the calibration curve. The results are shown in Table 4.

TABLE 4

| Amount of LPS (pg/ml) | RI | LPS content (pg/ml) |
|---|---|---|
| none | 20.7 | 0.01 |
| 1 | 83.3 | 0.99 |
| 2 | 149.0 | 2.02 |

Hitherto, the limit of determination of this type of LPS by Limulus test was the concentration of 1 pg/ml in a 0.5% aqueous phenylalanine solution, i.e., 200 pg per 1 g of the amino acid. On the other hand, as is clear from Table 4, LPS of 1 pg/ml in a 2% aqueous phenylalanine solution, i.e., 50 pg per 1 g of the amino acid can be determined according to the present invention. Thus, the sensitivity is extremely improved.

EXAMPLE 5

Measurement of the concentration of the pyrogen in an aqueous solution of methionine To a 5% aqueous methionine solution (30 ml) was added the adsorbent prepared in Reference Example 1 hereinafter (500 mg, wet weight) and the mixture was stirred at 50 r.p.m. at room temperature for 4 hours. Then, the adsorbent was removed to prepare a pyrogen-free aqueous methionine solution.

According to the same manner as that described in Example 4, LPS was added to the resulting solution to determine the pyrogen content. The results are shown in Table 5.

TABLE 5

| Amount of LPS (pg/ml) | RI | LPS content (pg/ml) |
|---|---|---|
| none | 26.9 | 0.11 |
| 1 | 84.9 | 1.02 |
| 2 | 148.0 | 2.01 |

In the case of an aqueous methionine solution, hitherto, the limit of determination of LPS content was 100 pg per 1 g of the amino acid. However, as is clear from Table 5, LPS of 1 pg/ml in a 5% aqueous methionine solution, i.e., 20 pg per 1 g of the amino acid can be determined according to the present invention. Thus, the sensitivity is extremely improved.

EXAMPLE 6

Measurement of the concentration of the pyrogen in an aqueous solution of cysteine hydrochloride A 0.25% aqueous cysteine hydrochloride solution hydrochloride was adjusted to pH 6.1 with sodium hydroxide and to the solution was added LPS to prepare aqueous cysteine hydrochloride solutions containing 1 pg/ml and 2 pg/ml of LPS, respectively.

According to the same manner as described in Example 4, LPS content was determined using the adsorbent prepared in Reference Example 1 hereinafter. Pyrogen-free water (3 ml) was used for washing the adsorbent. The results are shown in Table 6.

TABLE 6

| Amount of LPS (pg/ml) | RI | LPS content (pg/ml) |
|---|---|---|
| none | 16.3 | 0 |
| 1 | 69.8 | 1.04 |
| 2 | 118.0 | 2.05 |

In the case of an aqueous cysteine hydrochloride solution, hitherto, the limit of determination of LPS was 1000 to 2000 pg per 1 g of the amino acid. However, as is clear from Table 6, LPS of 1 pg/ml in a 0.25% cysteine hydrochloride solution, i.e., 400 pg per 1 g of the amino acid can be determined according to the present invention and sensitivity is extremely improved.

EXAMPLE 7

Measurement of the concentration of the pyrogen in an aqueous solution of penicillin G To a 1% aqueous solution of penicillin G (30 ml) was added the adsorbent prepared in Reference Example 1 hereinafter (1 g, wet weight) and the mixture was stirred at r.p.m. at room temperature for 4 hours. Then, the adsorbent was removed to give a pyrogen-free aqueous solution of penicillin G.

According to the same manner as described in Example 4, to the solution was added a predetermined amount of LPS and LPS content was determined using the adsorbent prepared in Reference Example 1 hereinafter. Pyrogen-free water (3 ml) was used for washing the adsorbent. The results are shown in Table 7.

TABLE 7

| Amount of LPS (pg/ml) | RI | LPS content (pg/ml) |
|---|---|---|
| none | 5.5 | 0.00 |
| 1 | 32.3 | 0.90 |

TABLE 7-continued

| Amount of LPS (pg/ml) | RI | LPS content (pg/ml) |
|---|---|---|
| 2 | 69.5 | 2.07 |

In the case of an aqueous solution of penicillin G, hitherto, the limit of determination of LPS was 200 pg per 1 g of penicillin G. However, as is clear from Table 7, LPS of 1 pg/ml in a 1% aqueous solution of penicillin G, that is, 100 pg per 1 g of penicillin G can be determined according to the present invention and sensitivity is extremely improved.

EXAMPLE 8

Operation for determining the pyrogen content according to the present invention To pyrogen-free water (3 ml) was added the predetermined amount of LPS (derived from $E.\ coli$ 0128: B12) and the mixture was stirred to prepare an aqueous solution of LPS (the concentration of LPS: 0, 10 and 20 pg/ml). To the solution was added the adsorbent prepared in Reference Example 1 hereinafter (100 mg, wet weight) and the mixture was stirred at 50 r.p.m. at room temperature for one hour. Then, it was centrifuged at 3000 r.p.m. for 5 minutes. To the adsorbent precipitated was added 0.2 M pyrogen-free Tris hydrochloride buffer (pH 8.0, 0.5 ml) containing 0.02 M magnesium chloride and the mixture was stirred and then allowed to stand for 30 minutes. After standing it was centrifuged and the concentration of LPS in the supernatant was determined according to Limulus method using a fluorescent synthetic substrate as follows.

The supernatant liquid was successively diluted with pyrogen-free water to give a sample solution. To the sample solution (100 μl) was added an solution of substrate (50 μl) and Limulus amebocyte lysate (50 μl) and the mixture was reacted at 37° C. for 90 minutes. The reaction was terminated by addition of a 12.5% aqueous acetic acid solution (2.3 ml) and then, according to the same manner as described in Example 1, relative intensity in fluorimetry was determined and LPS content was determined using LPS derived from $E.\ coli$ 0128: B12 as LPS standard. The results are shown in Table 8.

TABLE 8

| Run No. | LPS added (pg) | LPS measured (pg) |
|---|---|---|
| 1 | 0 | <0.1 |
| 2 | 0 | <0.1 |
| 3 | 30 | 26 |
| 4 | 30 | 36 |
| 5 | 60 | 41 |
| 6 | 60 | 62 |

As is clear from Table 8, LPS added was almost recovered to the supernatant eluted. Therefore, it is possible to measure the concentration of LPS by adsorbing it on the adsorbent and then eluting it.

EXAMPLE 9

Study on calibration curve

To a pyrogen-free phosphate buffer (pH 7.0, μ=0.02, 3 ml) was added a predetermined amount of LPS (derived from $E.\ coli$ 0128: B12) to prepare an aqueous solution of LPS (the concentration of LPS: 0, 5, 10 or 15 pg/ml). To the solution was added the adsorbent prepared in Reference Example 2 hereinafter (30 mg, wet weight) and the mixture was stirred at 50 r.p.m. at room temperature for one hour. Then, it was centrifuged at 3000 r.p.m. for 5 minutes. To the precipitate was added an aqueous solution of 0.4 mM Boc-Leu-Gly-Arg-MCA (50 μl) as an solution of substrate and Limulus amebocyte lysate [prepared by dissolving 1 vial (for 0.2 ml, sensitivity: gelled at 0.1 ng/ml as FDA reference endotoxin EC-2 concentration) of Limulus single test Wako (manufactured by Wako Pure Chemical Industries, Ltd.) into 0.4 M Tris hydrochloride buffer (pH 8.0, 1.5 ml) containing 0.04 M magnesium chloride] (50 μl) and the mixture was reacted at 37° C. for 20 minutes. After completion of the reaction, a 12.5% aqueous acetic acid solution (2.3 ml) was added to terminate the reaction and centrifuged at 3000 r.p.m. for 5 minutes. Then, fluorimetry was carried out at 380 nm of excitation wavelength and 460 nm of fluorescent wavelength. The results are shown in Table 9.

Figure 2:
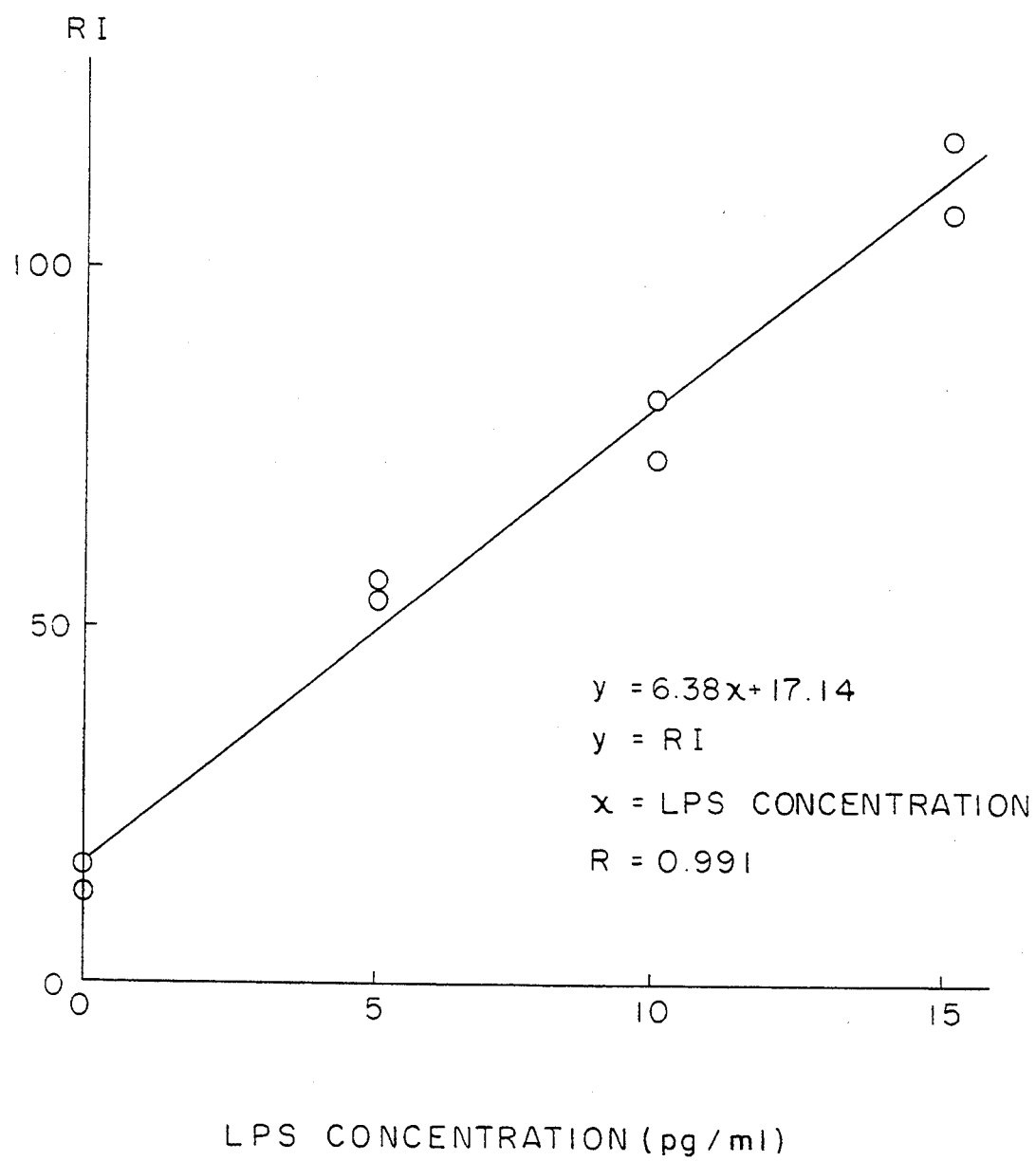

The resulting data were plotted on a graph wherein ordinates indicated a relative intensity (RI) in fluorimetry and abscissas indicated LPS concentration to obtain the calibration curve as shown in FIG. 2. The curve of FIG. 2 has a good linear relationship even in the low LPS concentration region.

TABLE 9

| Run No. | LPS concentration (pg/ml) | RI |
| --- | --- | --- |
| 1 | 0 | 12.9 |
| 2 | 0 | 16.1 |
| 3 | 5 | 52.8 |
| 4 | 5 | 56.2 |
| 5 | 10 | 73.7 |
| 6 | 10 | 82.0 |
| 7 | 15 | 108 |
| 8 | 15 | 118 |

EXAMPLE 10

Study on calibration curve

According to the same manner as described in Example 9, fluorimetry was carried out except that the adsorbent prepared in Reference Example 3 hereinafter was used in place of that prepared in Reference Example 2. The results are shown in Table 10.

Figure 3:
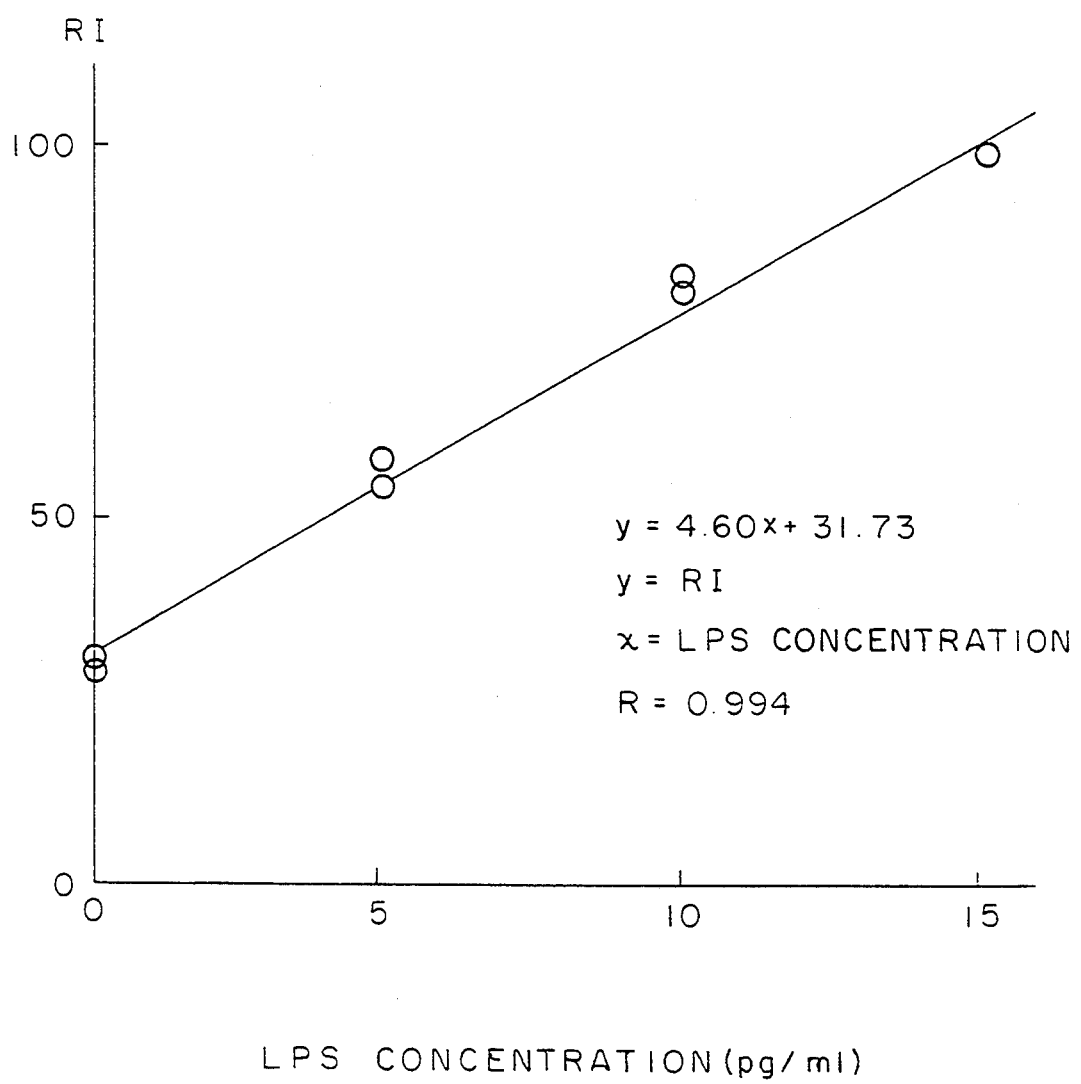

The resulting data were plotted on a graph wherein the ordinates indicated a relative strength (RI) in fluorimetry and the abscissas indicated LPS concentration to obtain a calibration curve as shown in FIG. 3. The curve of FIG. 3 shows a good linear relationship even in the low LPS concentration region.

TABLE 10

| Run No. | LPS concentration (pg/ml) | RI |
| --- | --- | --- |
| 1 | 0 | 29.0 |
| 2 | 0 | 30.4 |
| 3 | 5 | 54.1 |
| 4 | 5 | 57.8 |
| 5 | 10 | 82.3 |
| 6 | 10 | 80.5 |
| 7 | 15 | 97.8 |
| 8 | 15 | 98.5 |

Reference Example 1

(1) Sepharose CL-4B (trade name of an agarose derivative manufactured by Pharamacia Fine Chemicals, 30 g, wet weight) was suspended in a distilled water. 2N Aqueous sodium hydroxide (200 ml) and epichlorohydrin (50 ml) were added and the mixture was stirred at 40° C. for 2 hours. After completion of the reaction, the mixture was filtered and the residue was washed with a distilled water to obtain epichlorohydrin-activated Sepharose CL-4B. Epichlorohydrin-activated Sepharose CL-4B thus obtained was suspended in a 0.6% aqueous solution of hexamethylenediamine (1.4 liters) which had been warmed to 60° C. and the suspension was stirred at 60° C. for 2 hours. After completion of the reaction, the mixture was filtered and the residue was washed with a distilled water to give 3-(6-aminohexylamino)-2-hydroxypropylated Sepharose CL-4B (370 g, wet weight). When the aminohexyl content of the resulting Sepharose was measured by titration, it was about 37.6 μmol/g (wet weight).

(2) 3-(6-Aminohexylamino)-2-hydroxy-propylated Sepharose CL-4B (370 g, wet weight) was suspended in 4N aqueous sodium hydroxide (700 ml). Epichlorohydrin (700 ml) was added to the suspension at 65° C. and the mixture was stirred. After the temperature of the mixture was reached 90° C., it was stirred for additional 8 minutes. After completion of the reaction, water was added to the mixture to cool to 50° C. or lower. Then, the mixture was filtered, and the residue was washed with a distilled water to give epichlorohydrin-activated 3-(6-aminohexylamino)-2-hydroxypropylated Sepharose CL-4B. This was suspended in an aqueous solution of 20% histidine hydrochloride hydrate (adjusting to pH 12 with an aqueous sodium hydroxide, 2.1 liters) which had been heated to 90° C. and the suspension was stirred at 80° to 90° C. for 30 minutes. After completion of the reaction, the mixture was filtered and the residue was thoroughly washed with distilled water. The residue was suspended in distilled water (1 liter) and subjected to autoclaving at 120° C. for 20 minutes and then filtered. The residue was thoroughly washed in turn with 0.2N aqueous hydrochloric acid, 0.2N aqueous sodium hydroxide, 1.5 M aqueous sodium chloride and distilled water. Thus, water-insoluble adsorbent containing agarose as a carrier, histidine as a ligand and hexamethylenediamine as a spacer center (390 g, wet weight) was obtained. The content of histidine per 1 g (wet weight) of the adsorbent was 20.4 μmol.

Reference Example 2

The same procedure as described in Reference Example 1 was repeated except that Cellulofine GCL-2000-m (trade name of a cellulose derivative manufactured by Chisso Co., Ltd., 350 g) was used in place of Sepharose CL-4B. Thus, the water-insoluble adsorbent containing cellulose as a carrier, histidine as a ligand and hexamethylenediamine as a spacer center (340 g, wet weight) was obtained. The content of histidine per 1 g (wet weight) of the adsorbent was 58 μmol.

Reference Example 3

3-(6-Aminohexylamino)-2-hydroxy-propylated Sepharose CL-4B prepared according to the same manner as that described in Reference Example 1 (18 g, wet weight) was suspended in 0.05 M phosphate buffer (pH 7.0, 45.6 ml). A 25% aqueous solution of glutaraldehyde (19.2 ml) was added to the suspension and the mixture was stirred at room temperature for 2 hours. After completion of the reaction, the mixture was filtered and the residue was thoroughly washed with 0.1 M phosphate buffer (pH 7.0) to obtain glutaraldehyde-activated 3-(6-aminohexylamino)-2-hydroxy-propylated Sepharose CL-4B. This was suspended in 15 mM histamine-0.1 M phosphate buffer (pH 7.0, 59.6 ml) and the suspension was stirred at room temperature for 2 hours. After completion of the reaction, the mixture was filtered, and the residue was washed with a 1 M aqueous solution of sodium chloride (600 ml). The residue was suspended in 0.1 M phosphate buffer (pH 7.0, 30 ml). Sodium borohydride (0.3 g) was added to the suspension and the mixture was stirred at room temperature for an hour. After completion of the reaction, the mixture was filtered and the residue was thoroughly washed with 1 M aqueous sodium chloride solution and distilled water. Thus, water-insoluble adsorbent containing agarose as a carrier, histamine as a ligand and hexamethylenediamine as a spacer center (20.7 g, wet weight) was obtained. The content of histamine per 1 g (wet weight) of the adsorbent was 4.1 $\mu$mol.

What is claimed is:

1. A method for the detection of the presence of a pyrogen in a specimen, which comprises bringing the specimen into contact with an adsorbent composed of a nitrogen-containing heterocyclic compound said compound being histidine, or adenine, bonded to agarose through hexamethylenediamine, and, without eluting the pyrogen adsorbed ont he adsorbent, detecting whetehr there is any adsorbed pyrogen on the adsorbent by directly subjecting the adsorbent to a Limulus test.

2. A method according to claim 1, wherein the specimen is a water-containing solution or an aqueous solution.

3. A method according to claim 1, wherein the adsorbent is the nitrogen-containing heterocyclic compound bonded to the agarose through hexamethylenediamine by epichlorohydrin.

4. A method according to claim 1, wherein the adsorbent is histidine bonded to agarose through hexamethylenediamine.

5. A method according to claim 1, wherein the adsorbent is adenine bonded to agarose through hexamethylenediamine.

* * * * *